(12) United States Patent
Huang

(10) Patent No.: US 7,625,911 B2
(45) Date of Patent: Dec. 1, 2009

(54) AMORPHOUS FORM OF ERLOTINIB HYDROCHLORIDE AND ITS SOLID AMORPHOUS DISPERSION

(75) Inventor: Le Huang, Shang Gao (CN)

(73) Assignee: Mai De Ltd., Northborough, MA (US)

( * ) Notice: Subject to any disclaimer, the term of this patent is extended or adjusted under 35 U.S.C. 154(b) by 658 days.

(21) Appl. No.: 11/033,523

(22) Filed: Jan. 12, 2005

(65) Prior Publication Data
US 2006/0154941 A1    Jul. 13, 2006

(51) Int. Cl.
*A61K 31/517* (2006.01)
*C07D 239/94* (2006.01)

(52) U.S. Cl. .................... 514/266.4; 544/293
(58) Field of Classification Search ............... 514/266.4; 544/293
See application file for complete search history.

(56) References Cited

U.S. PATENT DOCUMENTS

| | | | |
|---|---|---|---|
| 5,747,498 A * | 5/1998 | Schnur et al. | 514/266.4 |
| 6,476,040 B1 * | 11/2002 | Norris et al. | 514/266.4 |
| 6,627,426 B2 * | 9/2003 | Biddle et al. | 435/243 |
| 6,900,221 B1 * | 5/2005 | Norris et al. | 514/266.4 |

2004/0162300 A1    8/2004 Bubendorf et al.

FOREIGN PATENT DOCUMENTS

WO   WO96/30347   3/1996
WO   WO01/34574   5/2001

OTHER PUBLICATIONS

Roche, Tarceva Product Information, Apr. 7, 2006, pp. 1-13.*
Corrigan, D.J. et. al., "Amorphous spray-dried . . . ", J. Pharm. Pharmacol., 1984, vol. 36, pp. 217-221.*
Duncan, Q.M. et. al., "The relevance of the amorphous state . . . ", Intl. J. of Pharmaceutics, 1999, vol. 179, pp. 179-207.*
Kai, T. et. al., "Oral Absorption Improvement . . . ", Chem. Pharm. Bull., 1996, vol. 44(3), pp. 568-571.*
Kawashima, Y. et. al., "Improvement of solubility and dissolution . . . ", J. Pharm. Pharmac., 1975, vol. 27, pp. 1-5.*

* cited by examiner

*Primary Examiner*—James O. Wilson
*Assistant Examiner*—Tamthom N Truong

(57) ABSTRACT

The present invention relates to novel amorphous form of [6,7-Bis(2-methoxy-ethoxy)-quinazolin-4-yl]-(3-ethynyl-phenyl) (erlotinib hydrochloride), to solid amorphous dispersion of erlotinib hydrochloride and a carrier such as PVP or solid PEG, to processes for their preparations, to pharmaceutical compositions containing them and to method of treatment using the same. The amorphous form or solid amorphous dispersion of erlotinib hydrochloride obtained in this invention is useful in preparing pharmaceutical dosage forms.

17 Claims, 2 Drawing Sheets

AMORPHOUS FORM OF ERLOTINIB HYDROCHLORIDE AND ITS SOLID AMORPHOUS DISPERSION

FIELD OF THE INVENTION

The present invention is directed to novel amorphous form of erlotinib hydrochloride and solid amorphous dispersion of erlotinib hydrochloride and a carrier such as PVP and solid PEG. The invention also relates to processes for preparing them, to pharmaceutical compositions containing them, and to method of treatment using the same.

BACKGROUND OF THE INVENTION

Erlotinib hydrochloride is the common chemical name of [6,7-bis(2-methoxy-ethoxy)-quinazolin-4-yl]-(3-ethynyl-phenyl) amine hydrochloride, a human epidermal growth factor type/epidermal growth factor receptor (HER1/EGFR) tyrosine kinase inhibitor, and following represents its chemical structure:

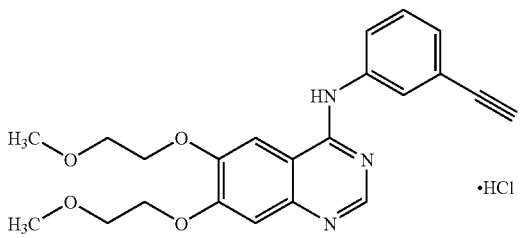

Erlotinib hydrochloride is the FDA approved drug for the treatment of non-small cell lung cancer. It has the potential for the treatment and/or prevention of diseases which are associated with tyrosine kinase enzymes such as epidermal growth factor receptors, such as cancer, particularly non small cell lung cancer, colorectal cancer, refractory non small cell lung cancer, pancreatic cancer, ovarian cancer, breast cancer, glioma, head cancer or neck cancer.

In WO 96/30347, the preparation of [6,7-Bis-(2-methoxy-ethoxy)-quinazolin-4-yl]-(3-ethynyl-phenyl)amine hydrochloride (erlotinib hydrochloride) as well as the uses of this compound for the treatment of hyperproliferative diseases have been disclosed. As described in Example 20, the erlotinib hydrochloride was prepared by dissolving the corresponding free base in $CHCl_3$ and ether, and titrated with 1M HCl in ether to precipitate the product as its hydrochloride salt. The obtained product has a melting point of 228-230° C., which is similar to that of polymorph form B of erlotinib hydrochloride, as described in Example 4 of a publication US2004/0162300.

Recently, two different polymorph forms of [6,7-bis(2-methoxy-ethoxy)-quinazolin-4-yl]-(3-ethynyl-phenyl) amine hydrochloride, designated as polymorph form A and polymorph form B, have been disclosed in WO 01/34574. As described in Example 4 and 5 of this publication, pure polymorph form A and pure polymorph form B or a mixture of polymorph form A and form B of erlotinib hydrochloride were made according to its procedures.

The preparation of a third polymorphic form of erlotinib hydrochloride, designed as polymorph form E, has been disclosed in US2004/0162300. As described in Example 1 of this publication, only crystal material (polymorph form E) of erlotinib hydrochloride was obtained.

All of references cited above did not mention or disclose amorphous forms of erlotinib hydrochloride.

The difference in many aspects of solid state properties such as solubility, dissolution and bioavailability of crystal (polymorphic) forms and amorphous forms of a given drug substance has been widely reported. The amorphous forms in a number of drugs exhibit superior dissolution characteristics and in some cases different bioavailability patterns compared to crystalline forms [Konne T., Chem Pharm Bull, 38, 2003 (1990)] were also noticed. For some therapeutic indications one bioavailability pattern may be favored over another. An amorphous form of cefuroxime axietil is good example for exhibiting much higher bioavailability than the crystalline forms, which leads to the selection of amorphous form as the final drug substance for cefuroxime axietil pharmaceutical dosage form development. In addition, since the physical and chemical stability of amorphous form can be improved by making solid amorphous dispersion containing drug substance and a carrier, the amorphous forms of most drug substances are therefore suitable for preparing solid pharmaceutical dosage forms.

SUMMARY OF THE INVENTION

We have now surprisingly and unexpectedly discovered that novel amorphous form of erlotinib hydrochloride or solid amorphous dispersion of erlotinib hydrochloride and a carrier such as PVP or solid PEG can be prepared.

In one aspect, the present invention relates to novel amorphous form of [6,7-bis(2-methoxy-ethoxy)-quinazolin-4-yl]-(3-ethynyl-phenyl)amine hydrochloride (erlotinib hydrochloride), including anhydrous amorphous erlotinib hydrochloride as well as amorphous erlotinib hydrochloride hydrate.

In another aspect, the present invention relates to a process for preparing amorphous form of erlotinib hydrochloride, including the steps of dissolving crystalline erlotinib hydrochloride in a suitable solvent(s) and removing the solvent(s) from the solution by a conventional technique to afford amorphous form of erlotinib hydrochloride. Such conventional techniques include, but are not limited to, distillation, distillation under reduced pressure or vacuum, evaporation and spray drying.

In a preferred aspect, the present invention relates to a process for preparing amorphous form of erlotinib hydrochloride, including the steps of dissolving crude or pure crystalline erlotinib hydrochloride in a suitable solvent(s) such as methanol or ethanol to form a solution and distilling the solvent from the solution to afford amorphous form of erlotinib hydrochloride and then drying the product.

In a more preferred aspect, the present invention relates to a process for preparing amorphous form of erlotinib hydrochloride, including the steps of dissolving crude or pure crystalline erlotinib hydrochloride in methanol or ethanol to form a solution and using a spray drying technique to recover amorphous form of erlotinib hydrochloride and then drying the product.

In a further aspect, the present invention relates to a solid amorphous dispersion of erlotinib hydrochloride and a carrier. The carrier is selected from solid polyethylene glycol (PEG) and polyvinylpyrrolidone (PVP).

In a still aspect, the present invention relates to a process for preparing amorphous dispersion of erlotinib hydrochloride and a carrier, including the steps of dissolving crystalline erlotinib hydrochloride and a carrier in a suitable solvent(s) and removing the solvent(s) from the solution by distillation and spray drying.

Another aspect of the present invention is a pharmaceutical composition for administering effective amount of amorphous erlotinib hydrochloride or its amorphous dispersion in unit dosage form and a pharmaceutically acceptable excipient.

According to a further aspect of the invention is a method for prevention and treatment of cancer, particularly non small cell lung cancer, colorectal cancer, refractory non small cell lung cancer, pancreatic cancer, ovarian cancer, breast cancer, glioma, head cancer or neck cancer, with a medicament made by using an effective amount of novel amorphous form of erlotinib hydrochloride in unit dosage form.

BRIEF DESCRIPTION OF THE ACCOMPANYING DRAWINGS

DETAILED DESCRIPTION OF THE INVENTION

Unless otherwise indicated, the following definitions are set forth to illustrate and define the meaning and scope of the various terms used to describe the invention herein.

The term "crystalline polymorph" refers to a crystal modification that can be characterized by analytical methods such as X-ray powder diffraction, IR-spectroscopy, differential scanning calorimetry (DSC) or by its melting point.

The term "amorphous" means a solid without long-range crystalline order. Amorphous form of erlotinib hydrochloride in accordance with the invention preferably contains less than about 10% crystalline forms of erlotinib hydrochloride, preferably less than 5% crystalline from of erlotinib hydrochloride, and more preferably is essentially free of crystalline forms of erlotinib hydrochloride. "Essentially free of crystalline forms of erlotinib hydrochloride" means that no crystalline polymorph forms of erlotinib hydrochloride can be detected within the limits of a powder X-ray diffractometer.

The term "amorphous dispersion" means a solid composite comprising amorphous erlotinib hydrochloride homogeneously dispersed in a pharmaceutically acceptable carrier (or excipient) which is also in an amorphous state. The ratio of erlotinib hydrochloride to a carrier (or excipient) in terms of weight is from 1% to 300%, preferably 10-50%.

The term "carrier" in this invention means solid polyethylene glycol (PEG) or polyvinylpyrrolidone (PVP) in amorphous state.

The term "pharmaceutically acceptable" means that which is useful in preparing a pharmaceutical composition that is generally non-toxic and is not biologically undesirable and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions of the present invention encompass any composition made by admixing the active ingredient, active ingredient dispersion or composite, additional active ingredient(s), and pharmaceutically acceptable excipients.

Crude or pure crystalline erlotinib hydrochloride compound itself may be prepared according to known procedures such as those disclosed in U.S. Pat. Publication 2004/0162300, WO96/30347 and WO01/34574, of which the disclosures are incorporated herein by reference.

Figure 1:
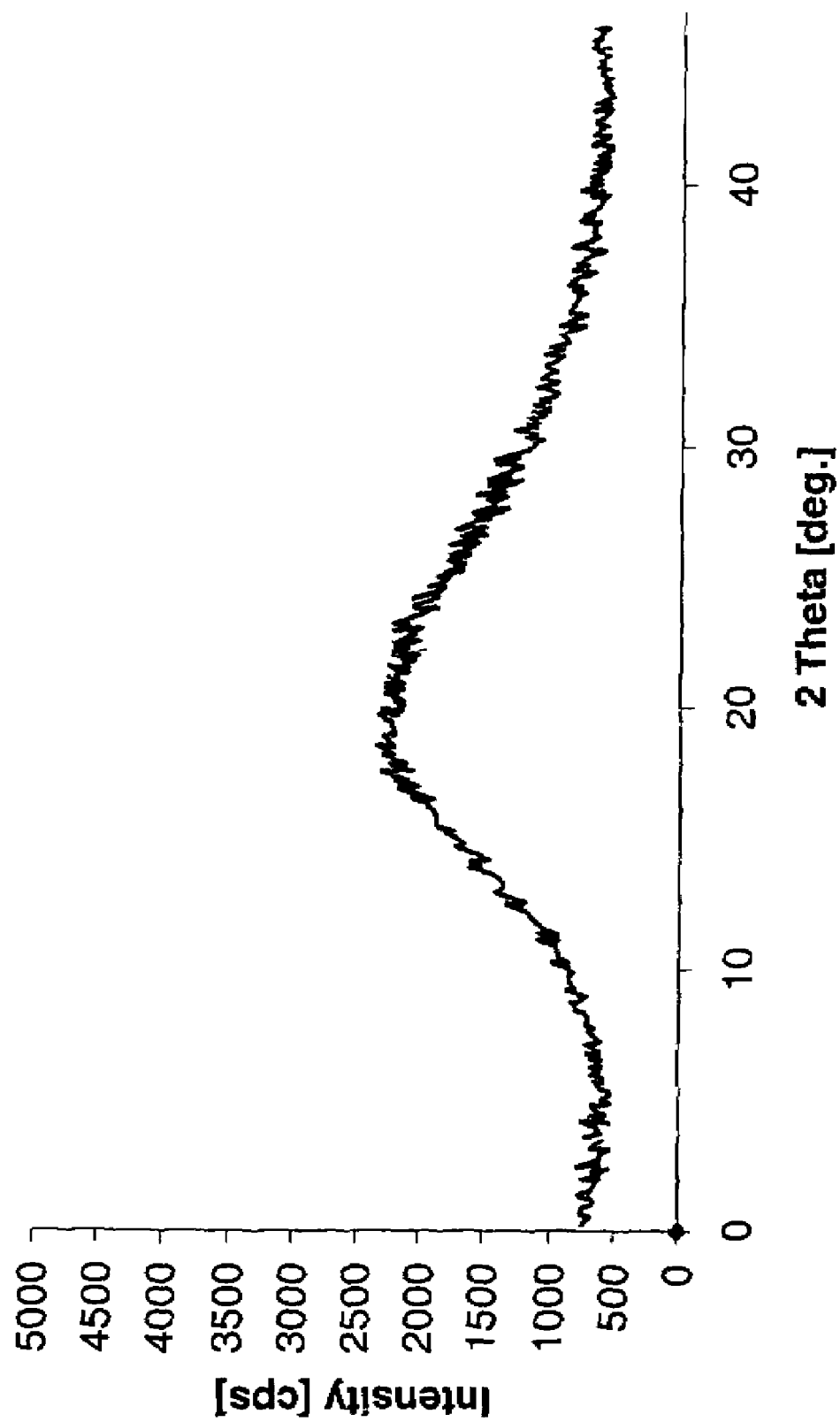
FIG. 1 is X-ray powder diffraction pattern of amorphous form of erlotinib hydrochloride.

According to one aspect of the invention, this invention provides novel amorphous form of [6,7-Bis-(2-methoxy-ethoxy)-quinazolin-4-yl]-(3-ethynyl-phenyl)amine hydrochloride (erlotinib hydrochloride). Amorphous materials do not exhibit the three-dimensional long-range order found in crystalline materials but are structurally more similar to liquids where the arrangement of molecules is random. Amorphous solids are not crystalline and therefore do not give a definitive x-ray diffraction pattern (XRD). In addition, they do not give rise to a melting point or endothermic or exothermic peaks in DSC and tend to liquefy at some point beyond the glass transition point. A sample of XRD spectra of erlotinib hydrochloride obtained by the inventor is shown in FIG. 1, which demonstrated that the XRD pattern is highly characteristic of an amorphous solid.

In another aspect, the present invention provides a process of preparing a novel amorphous form of [6,7-bis-(2-methoxy-ethoxy)-quinazolin-4-yl]-(3-ethynyl-phenyl)amine hydrochloride (erlotinib hydrochloride).

In a preferred aspect, the present invention also provides a distillation process for preparing amorphous form of erlotinib hydrochloride, including the steps of dissolving crystalline erlotinib hydrochloride in a solvent to form a solution and distilling the solvent from the solution to dryness to afford amorphous form of erlotinib hydrochloride and further drying the product.

In a first step of the distillation process, crystalline erlotinib hydrochloride is preferably dissolved in an aqueous solvent; more preferably dissolved in a straight or branched chain $C_1$-$C_4$ alcohol solvent, and most preferably dissolved in methanol or ethanol to form a solution. Erlotinib hydrochloride has the highest solubility in methanol or ethanol, allowing the complete dissolution of erlotinib hydrochloride at elevated temperature.

In particular, erlotinib hydrochloride is soluble in methanol at or over 50° C., allowing the complete dissolution of erlotinib hydrochloride in methanol at 50° C. or above with a concentration of 10 mg per milliliter (ml). The use of a relatively concentrated solution, e.g. about 10 mg per ml is therefore preferred for methanol.

In particular, erlotinib hydrochloride is soluble in ethanol at or over 70° C., allowing the complete dissolution of erlotinib hydrochloride in ethanol at ambient temperature with a concentration of 10 mg per ml. The use of a relatively concentrated solution, e.g. about 10 mg per ml is therefore preferred for ethanol.

In a second step of the distillation process, using conventional distillation methods, the solvent is removed from the solution to dryness, thereby leaving a solid residue containing amorphous erlotinib hydrochloride and further drying the product under vacuum.

The distillation process can be preformed at atmospheric pressure or reduced pressure. Preferably the solvent is removed at a pressure of about 760 mm Hg or less, more preferably at about 400 mm Hg or less, more preferably at about 80 mm Hg or less, and most preferably from about 30 to about 80 mm Hg.

The removal of the solvent from the erlotinib hydrochloride solution may be carried out at an increased temperature, preferably at reflux temperature. Preferably, the removal of the solvent may be carried out preferably below 75° C., more preferably at about 40° C.-75° C., yet more preferably at about 60° C.-75° C., yet more preferably at about 65° C.-70° C. The solid residue obtained after solvent removal may be isolated and further dried using conventional methods.

The straight or branched chain $C_1$-$C_4$ alcohol solvents are selected from methanol, ethanol, n-propanol, isopropanol or branched-chain butanols. It is preferred to use methanol or ethanol, or a mixture of methanol and ethanol. The process may also be carried out by using a mixture of two or more other alcohol solvents.

In a more preferred aspect, the present invention also provides a process for preparing amorphous form of erlotinib hydrochloride, including the steps of dissolving crystalline erlotinib hydrochloride in methanol or ethanol to form a solution and using a spray drying technique to recover amorphous form of erlotinib hydrochloride.

In particular, erlotinib hydrochloride is soluble in methanol, ethanol or a mixture of ethanol and water solvents at 45° C.-55° C., allowing the complete dissolution of erlotinib hydrochloride in methanol or ethanol at this elevated temperature with a concentration of about 10 mg per ml. The use of a relatively concentrated solution, e.g. about 10 mg per ml or over is therefore preferred for spraying drying process.

The spray drying process can be carried out using any commercially available dryers, which are used, operates on the principle of nozzle spraying in a parallel flow. For instance, the sprayed product and drying gas flow in the same direction. The drying gas can be air or inert gasses such as nitrogen, argon and carbon dioxide. Nitrogen gas is preferred in this invention. For erlotinib hydrochloride solution, the spray drying in-let temperature is about 80-100° C., and the out-let temperature is about 60-35° C. at a feed rate of 5-25 m/min.

The product obtained from above processes (distilling and spray drying) may further be dried to achieve the desired moisture and solvent(s) residue values. It may be dried in a tray drier or dried under vacuum or in a Fluid Bed Dryer. In this invention, the obtained amorphous form of erlotinib hydrochloride is further dried under vacuum in fluid bed drier for 12-15 hours at 40° C. or below.

The novel amorphous forms of erlotinib hydrochloride obtained in above procedures can be anhydrous amorphous erlotinib hydrochloride and amorphous erlotinib hydrochloride hydrate. The current invention intends to cover both anhydrous and hydrate amorphous forms of erlotinib hydrochloride.

It has been unexpectedly found that uniformly anhydrous or hydrate amorphous forms of erlotinib hydrochloride can be obtained in simple and reproducible processes as described above.

In still another aspect, the present invention provides a solid amorphous dispersion of erlotinib hydrochloride and a carrier. The carrier for preparing such solid amorphous dispersion is in an amorphous state or has been converted into amorphous state, and is selected from a group of pharmaceutically acceptable excipients consisting of solid polyethylene glycol (PEG) or polyvinylpyrrolidone (PVP). The weight ratio of erlotinib hydrochloride to a carrier is 1%-300%, preferably 5-100%, and most preferably 10-30%.

In still further aspect, the present invention provides a process to prepare a solid amorphous dispersion of erlotinib hydrochloride and a carrier, including the steps involve: 1) dissolving erlotinib hydrochloride in methanol, ethanol or a mixture of water and ethanol to form a solution; 2) dissolving carrier in methanol, ethanol or a mixture of water and ethanol to form a solution; 3) adding the erlotinib hydrochloride solution to the carrier solution [or alternatively for 2 and 3 steps erlotinib hydrochloride can be added directly into the solvent containing the carrier]; 4) stirring the resulting solution; 5) evaporating the solvent from the solution to dryness by distilling or spray drying technique, drying the product to afford amorphous dispersion of erlotinib hydrochloride and a carrier, and further grinding and drying the product.

In a preferred aspect, the distillation process for preparing amorphous dispersion of erlotinib hydrochloride and a carrier, including the steps of dissolving amorphous or crystalline erlotinib hydrochloride and a carrier in methanol, ethanol or a mixture of water and ethanol to form a solution and distilling the solvent from the solution under reduced pressure such as 400 mmHg or less, preferable 80 mmHg, most preferably 30-80 mmHg, to dryness to afford solid amorphous dispersion of erlotinib hydrochloride and further drying the product. Further details can be found in Examples.

The spray drying process for preparing amorphous dispersion of erlotinib hydrochloride and a carrier can be carried out using any commercially available dryers, which are used, operates on the principle of nozzle spraying in a parallel flow. For instance, the sprayed product and drying gas flow in the same direction. The drying gas can be air or inert gasses such as nitrogen, argon and carbon dioxide. Nitrogen gas is preferred in this invention. Amorphous or crystalline erlotinib hydrochloride and a carrier is dissolved in methanol, ethanol or a mixture of water and ethanol to form a solution and spay drying the solvent from the solution to afford a white off solid powder as amorphous dispersion of erlotinib hydrochloride and a carrier, and further drying the product. The spray drying in-let temperature is about 140-170° C., and the out-let temperature is about 70-90° C. at a feed rate of 5-25 ml/min. Further details can be found in Examples.

The solid amorphous dispersion product obtained from distilling and spray-drying technique may further be dried to achieve the desired moisture and solvent(s) residue values. It may be dried in a tray drier or dried under vacuum or in a Fluid Bed Dryer. In this invention, the obtained amorphous form of erlotinib hydrochloride is further dried under vacuum in fluid bed drier for 12-15 hours at 40° C. or below. The carrier for a process of preparing such solid amorphous dispersion by distilling or spray drying is selected from a group of pharmaceutically acceptable excipients consisting of solid polyethylene glycol (PEG) or polyvinylpyrrolidone (PVP).

Figure 2:
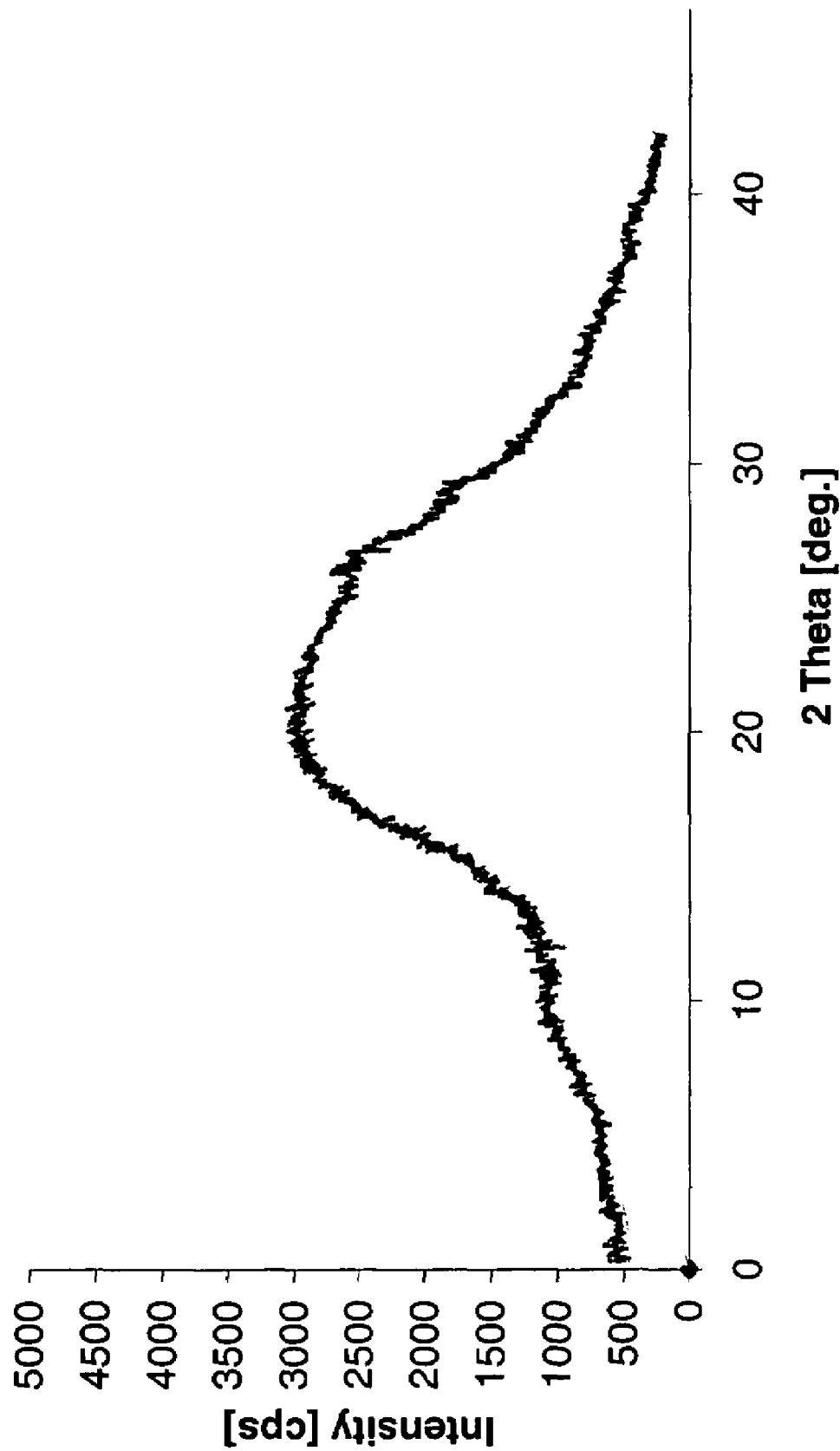
FIG. 2 is X-ray powder diffraction pattern of amorphous dispersion of erlotinib hydrochloride and PEG (8000).

Amorphous form of erlotinib hydrochloride and its solid amorphous dispersion prepared according to the processes of the present invention may be characterized by its x-ray powder diffraction pattern, as shown in the accompanied drawing of FIG. 1 and FIG. 2. The X-ray powder diffraction pattern (FIG. 1 and FIG. 2) shows no peaks that are characteristic of amorphous erlotinib hydrochloride and its solid amorphous dispersion, thus demonstrating the amorphous nature of the product.

The invention further relates to a composition of solid erlotinib hydrochloride wherein at least 85% of the total weight of erlotinib hydrochloride is in the amorphous form. In a preferred form of this composition, the solid erlotinib hydrochloride is suitable for use as a bulk active ingredient in formulating pharmaceutical products. The remainder of the solid erlotinib hydrochloride in the composition, i.e., 15% or less of the total weight of erlotinib hydrochloride, may be other forms of erlotinib hydrochloride, e.g. crystalline forms or polymorphs.

In a preferred aspect of the invention, the composition may include at least 95% of the amorphous form of erlotinib hydrochloride with respect to total weight of the solid erlotinib hydrochloride in the composition. In another aspect of the invention, the composition may include at least 99% of the amorphous form of erlotinib hydrochloride with respect to total weight of the solid erlotinib hydrochloride in the composition. In yet more preferred aspect of the invention, the composition is substantially free of any crystalline forms or polymorphs of erlotinib hydrochloride other than its amorphous form.

The preferred method of differentiating amorphous erlotinib hydrochloride from other crystalline and non-crystalline forms of erlotinib hydrochloride is X-ray powder diffraction (XPD). The XPD pattern of pure amorphous erlotinib hydrochloride, as illustrated in FIG. 1, can be seen to lack discernible acute peaks. Thus, amorphous erlotinib hydrochloride, according to the present invention, is characterized in providing an X-ray powder diffraction pattern containing one or more broad diffuse halos having very low counts (i.e. see FIG. 1) in contrast to the sharp diffraction peaks characteristic of crystalline materials. Of course it will be appreciated that a mixture comprising detectable amounts of both crystalline and amorphous erlotinib hydrochloride will exhibit both the characteristic sharp peaks and the diffuse halo(s) on XPD. This will be evident by an increase in the baseline and also a reduction in crystalline peak intensities.

X-ray diffraction also provides a convenient and practical means for quantitative determination of the relative amounts of crystalline and/or amorphous forms in a solid mixture. X-ray diffraction is adaptable to quantitative applications because the intensities of the diffraction peaks of a given compound in a mixture are proportional to the fraction of the corresponding powder in the mixture. Therefore, the percent composition of amorphous or crystalline forms of erlotinib hydrochloride in an unknown composition can be determined by using standard calibration curve, which can be constructed by spiking known amount of pure crystalline form into amorphous erlotinib hydrochloride to determine the percent ratio of a particular crystalline form. For example, five or more artificial mixtures of crystalline forms of erlotinib hydrochloride, at different amounts, may be prepared. In a non-limiting example, such mixtures may contain, 1%, 3%, 5%, 7%, and 10% of erlotinib hydrochloride for each crystalline form. Preferably, the measurements are made on solid powder erlotinib hydrochloride. This is done by comparing the relative intensities of the peaks from the diffraction pattern of the unknown solid powder composition with a calibration curve derived from the X-ray diffraction patterns of pure known samples. The limits of detection of a particular form in admixture with another form, i.e. crystalline in amorphous or vice versa, by XPD method is reported to be approximately 5% according to Hancock and Zografi (J. Pharm. Sci., 86:1-12, 1997).

In addition to X-ray powder diffraction, amorphous erlotinib hydrochloride, or the presence of some amorphous erlotinib hydrochloride, can be distinguished from crystalline erlotinib hydrochloride, using Raman spectroscopy, solution calorimetry, differential scanning calorimetry, solid state nuclear magnetic resonance spectra (ssNMR) or infra-red spectroscopy. Each of these techniques is well established in the art. Amorphous erlotinib hydrochloride can also be identified based on the morphology of the particles seen under an electron microscope. Furthermore, amorphous erlotinib hydrochloride is likely to be much more soluble than crystalline erlotinib hydrochloride because the former is lack of lattice energy, providing another means of discriminating between the crystalline and amorphous erlotinib hydrochloride forms, or detecting an amount of amorphous form within a erlotinib hydrochloride preparation. As noted above, the preferred method of differentiating amorphous erlotinib hydrochloride from other crystalline and non-crystalline forms of erlotinib hydrochloride is X-ray powder diffraction (XPD).

It will be appreciated that because of the enhanced solubility property of amorphous erlotinib hydrochloride, mixtures comprising substantially crystalline or other solid forms of erlotinib hydrochloride with amorphous erlotinib hydrochloride will, depending on the amount of amorphous product present, may also possess varying degrees of increased solubility. Such mixtures comprising amorphous erlotinib hydrochloride can be prepared, for example, by mixing amorphous erlotinib hydrochloride prepared according to the present invention with other solid forms of erotinib hydrochloride, such as crystalline form, prepared according to prior art methods. A mixture might also be prepared if the manufacturing process is incomplete, or incorporates steps that allow or cause amorphous product to be formed.

Another embodiment of the present invention is a pharmaceutical composition for administering effective amount of amorphous erlotinib hydrochloride as active ingredient in unit dosage forms. The amorphous erlotinib hydrochloride can be amorphous form of erlotinib hydrochloride or its solid amorphous dispersion. Both materials are well suited to be used for making the pharmaceutical composition such as tablets and capsules.

The unit dosage forms can be administered in a wide variety of oral and parenteral dosage forms. Thus, the compound of the present invention can be administered by injection, that is, intravenously, intramuscularly, intracutaneously, subcutaneously, intraduodenally, or intraperitoneally. Also, the amorphous form of erlotinib hydrochloride of the present invention can be administered by inhalation, for example, intranasally. Additionally, the compound of the present invention can be administered transdermally. It will be obvious to those skilled in the art that the following dosage forms may comprise as the active component, either amorphous form of erlotinib hydrochloride, or a corresponding pharmaceutically acceptable salt of a compound of the present invention.

For preparing pharmaceutical compositions from amorphous form of erlotinib hydrochloride or its solid amorphous dispersion of the present invention, pharmaceutically acceptable excipients can be either solid or liquid.

Solid form compositions include powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or an encapsulating material.

In powders, the excipient is a finely divided solid that is in a mixture with the finely divided active component. In tablets, the active component is mixed with the carrier having the necessary binding properties in suitable proportions and compacted in the shape and size desired.

The powders and tablets preferably contain from one or ten to about seventy percent of the active compound. Suitable carriers are magnesium carbonate, magnesium stearate, talc, sugar or lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, retention enemas, and emulsions, for example water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Also included are solid form compositions that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical composition is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 7000 mg, preferably 5 mg to 2000 mg, more preferably 5 to 200 mg according to the particular application and the potency of the active component. The composition can, if desired, also contain other compatible therapeutic agents. However, the optimum dosage for the individual subject being treated will be determined by the person responsible for treatment, generally smaller doses being administered initially and thereafter increments made to determine the most suitable dosage.

In a preferred aspect of the invention, the pharmaceutical composition conveniently contain about 1-1000 mg, preferably 5-200 mg of amorphous erlotinib hydrochloride as active ingredient.

According to a further aspect of the invention is a method of treating a cancer's disease condition, which comprises administering to warm-blooded mammal, particularly a human, and effective amount of an amorphous form of erlotinib hydrochloride. As a human epidermal growth factor type/epidermal growth factor receptor (HER1/EGFR) tyrosine kinase inhibitor, amorphous form of erlotinib hydrochloride or solid amorphous dispersion of erlotinib hydrochloride and a carrier such as PVP and solid PEG can be used in the prevention and the treatment of diseases which are associated with tyrosine kinase enzymes such as epidermal growth factor receptors, such as cancer, particularly non small cell lung cancer, colorectal cancer, refractory non small cell lung cancer, pancreatic cancer, ovarian cancer, breast cancer, glioma, head cancer or neck cancer.

In therapeutic use as a human epidermal growth factor type/epidermal growth factor receptor (HER1/EGFR) tyrosine kinase inhibitor for treating cancer's disease, the amorphous form of erlotinib hydrochloride or solid amorphous dispersion of erlotinib hydrochloride and a carrier such as PVP and solid PEG utilized in the pharmaceutical composition of this invention is administered at the initial dosage of about 1 mg to about 500 mg of active ingredient daily. A daily dose range of about 25 mg to about 150 mg of active ingredient is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following examples are provided to illustrate specific embodiments of the present invention. They are not intended to be limiting in any way.

EXAMPLES

Example 1

Preparation of Amorphous Erlotinib Hydrochloride: Distilling Method

Example A

Crystalline erlotinib hydrochloride (1.6 g, obtained by the procedure described in Example 20 of WO 96/30347) was dissolved in methanol (160 ml) at ambient temperature, and suspension mixture was heated to 50° C. to obtain a clear solution. The solution was then heated at reflux temperature. The solvent was evaporated through distillation under vacuum (30-80 mm Hg) at about 60° C. to about 70° C. The product was then isolated (1.52 g, yield 95%) when no visible liquid was remained, and drying was continued under vacuum at about 40° C. for about 12 hour to remove the solvent. The powder X-ray diffractogram of the solid (FIG. 1) showed that the resulting substance was in amorphous form.

Example B

Crystalline erlotinib hydrochloride (1.6 g, obtained by the procedure described in Example 20 of WO 96/30347) was dissolved in ethanol (160 ml) at ambient temperature, and suspension mixture was heated to 70° C. to obtain a clear solution. The solution was then heated at reflux temperature. The solvent was evaporated through distillation under vacuum (30-80 mm Hg) at about 60° C. to about 70° C. The product was then isolated (1.46 g, yield 91%) when no visible liquid was remained, and drying was continued under vacuum at about 40° C. for about 12 hour to remove the solvent. The powder X-ray diffractogram of the solid (FIG. 1) showed that the resulting substance was in amorphous form.

Example 2

Preparation of Solid Amorphous Dispersion of Erlotinib Hydrochloride and PEG (8000): Distilling Method Amorphous erlotinib hydrochloride (2.0 g, obtained from Example 1 of this invention) and 10 g of polyethylene glycol (PEG, 8000) was dissolved in methanol (200 ml) at ambient temperature in a round bottom flask with the aid of magnetic stirring and sonication. The suspension mixture was heated to 60° C. to obtain a clear solution. The solvent was evaporated through distillation under vacuum (30-80 mm Hg) at about 60° C. to about 70° C. The product was then isolated when no visible liquid remained, and drying was continued under vacuum at about 40° C. for about 12 hour to remove the solvent. The dried material was then grounded into fine powder, and was further dried under vacuum at about 40° C. for 8 hours. The powder X-ray diffractogram of the solid (FIG. 2) showed that the resulting substance was in amorphous form.

Example 3

Preparation of Solid Amorphous Dispersion of Erlotinib Hydrochloride and PVP (K 30): Spray Drying Method Crystalline erlotinib hydrochloride (2.0 g, 1.6 g, obtained by the procedure described in Example 20 of WO 96/30347) and 10.0 g polyvinylpyrrolidone (PVP, K=30) was dissolved in 200 ml of ethanol and water (ethanol/water, 80:20, v/v) at ambient temperature in a round bottom flask, with the aid of magnetic stirring and sonication. The suspension mixture was heated to 60° C. to obtain a clear solution. The solution was cooled to 35° C., and then subjected to spray drying in a Mini-Spray Dryer (e.g., Buchi Model-190) at an inlet temperature 145-175° C. and outlet temperature 70-90° C. using nitrogen gas. The light-white fine powder of erlotinib hydrochloride and PVP in an amorphous form was obtained. The product was further dried under vacuum at about 40° C. for about 12 hour to afford 10.5 g of the desired solid amorphous product, as characterized by powder X-ray diffractogram or DSC.

Example 4

Preparation of Amorphous Erlotinib Hydrochloride: Spray Drying Method

Example A

Crystalline erlotinib hydrochloride (3.2 g, obtained by the procedure described in Example 20 of WO 96/30347) was dissolved in methanol (320 ml) at 48-52° C. to obtain a clear solution. The solution was cooled to 30° C., and then subjected to spray drying in a Mini-Spray Dryer (e.g., Buchi Model-190) at an inlet temperature 85-87° C. and outlet temperature 50-40° C. sing nitrogen gas. The light-white fine powder of erlotinib hydrochloride in an amorphous form was obtained. The product was further dried under vacuum at about 40° C. for about 12 hour to afford 3.0 g of the desired product (yield, 94%). The powder X-ray diffractogram of the solid (FIG. 1) showed that the resulting substance was in amorphous form.

Example B

Crystalline erlotinib hydrochloride (3.2 g, obtained by the procedure described in Example 4 and 5 of WO 01/34574) was dissolved in 320 ml of ethanol and water (ethanol/water, 80:20, v/v) at 48-52° C. to obtain a clear solution. The solution was cooled to 30° C., and then subjected to spray drying in a Mini-Spray Dryer (e.g., Buchi Model-190) at an inlet temperature 85-90° C. and outlet temperature 50-40° C. sing nitrogen gas. The light-white fine powder of erlotinib hydrochloride in an amorphous form was obtained. The product was further dried under vacuum at about 40° C. for about 12 hour to afford 2.9 g of the desired product (yield, 91%). The powder X-ray diffractogram of the solid (FIG. 1) showed that the resulting substance was in amorphous form.

Example 5

Preparation of Pharmaceutical Composition Containing Amorphous Erlotinib Hydrochloride and Solid Amorphous Dispersion Pharmaceutical compositions suitable for tablet dosage forms made using amorphous erlotinib hydrochloride and its amorphous dispersion and excipients are detailed in Table 1. Pharmaceutical compositions suitable for capsule dosage forms made using amorphous erlotinib hydrochloride and its amorphous dispersion and excipients are detailed in Table 2.

Compositions A and C listed in Table 1 provide a dose of 25 mg erlotinib hydrochloride in 300 mg tablet. Composition B listed in Table 1 provides a dose of 150 mg erlotinib hydrochloride in 550 mg tablet. Composition D and F listed in Table 2 provide a dose of 25 mg erlotinib hydrochloride in 255 mg capsule. Composition E listed in Table 2 provides a dose of 150 mg erlotinib hydrochloride in 515 mg capsule.

TABLE 1

Film coated tablets containing the following ingredients can be manufactured in a conventional manner:

| | Per tablet | | |
|---|---|---|---|
| Ingredients | A | B | C |
| Core: | | | |
| Amorphous erlonitib hydrochloride | 25 mg | 150 mg | — |
| Dispersion of erlotinib HCl (20%) and PVP | — | — | 125 mg |
| Mirocrystalline cellulose | 67.5 | 81.5 | 57.5 |
| Lactose anhydrous | 140.0 | 180.0 | 56.0 |
| Sodium starch glycolate | 35.0 | 80.0 | 24.0 |
| Pregelatinized starch | 30.0 | 90.0 | 15.0 |
| Magnesium stearate | 2.5 | 8.5 | 2.5 |
| (Total core weight, mg) | 300 | 550 | 300.0 |
| Film Coat: | | | |
| Hydroxypropyl methylcellulose | 5 mg | 9.0 mg | 5 mg |
| Polyetylene glycol 6000 | 1.0 mg | 1.6 mg | 1.0 mg |
| Talc | 1.5 mg | 2.5 mg | 1.5 mg |
| Iron oxide (yellow) | 1.0 mg | 1.5 mg | 1.0 mg |
| Titan dioxide | 1.0 mg | 1.5 mg | 1.0 mg |

There were three major steps involved in manufacturing the tablets: (1) preparation of erlotinib hydrochloride granular concentrate; (2) preparation of erlotinib hydrochloride tablet core; (3) coating the tablet core.

The active or active dispersion and following ingredients were sifted through a clean screen (typically 0.066"): lactose anhydrous, pregelatinized starch, sodium starch glycolate and microcrystalline cellulose.

The screened materials were transferred into a high shear (high-energy) mixer and blended for ten (10) minutes at 100 rpm. The blended material was granulated with purified water. The wet granules were passed through a screen (typically 0.132"), and dried in a fluid bed drier until loss on drying is less than 0.2-0.5% w/w. The dried granules were passed a screen (typically 0.039") and blended using a tumble blender for 10 minutes at 12 rpm.

The concentrated granules are placed into a tumble blender. About two thirds of the lactose is screened and added to the blender, and blended for ten (10) minutes. The microcrystalline cellulose, sodium starch glycollate, magnesium stearate and remaining lactose are screened and added to the blender. The mixtures are blended together for ten (10) minutes. The blended material was compressed on a Kikusui Libra tablet compression machine to a target weight of 300 mg for the 25 mg, and 550 mg for 150 mg tablets.

The tablet cores are then transferred to a tablet-coating machine (pan coater). The tablet bed was pre-heated with warm air (approximately 60° C.). The pan speed was

TABLE 2

Capsules containing the following ingredients can be manufactured in a conventional manner:

| Ingredients | Per capsule | | |
|---|---|---|---|
| | D | E | F |
| Amorphous erlonitib hydrochloride | 25 mg | 150 mg | — |
| Amorphous dispersion of erlotinib HCl (20%) and PVP (K30) | — | — | 125 mg |
| Lactose anhydrous | 200.0 | 350.0 | 100 |
| Microcrystalline cellulose (AVICEL PH 102) | 25.0 | 100.0 | 25 |
| Talc | 5 | 15 | 5 |
| Total (mg/capsule) | 255 | 515 | 255 | adjusted to 5-9 RPM before starting the spray cycle. The spray cycle was activated. The exhaust temperature was maintained between 40° C. and 50° C. throughout the cycle. After the proper amount of solution was applied, the coated tablets were dried for approximately two (2) minutes. Steps were repeated for all pans to coat all tablets in the batch and film coated until the tablet weight has increased by 2.0% to 4.5%. All tablets were packaged in plastic bottles with desiccants, and the bottles were heat sealed, then placed under the storage conditions.

The components for preparing capsules are sieved and mixed and filled into capsules of size 2 and 3.

While the present invention has been described in terms of its specific embodiments, certain modifications and equivalents will be apparent to those skilled in the art and are intended to be included within the scope of the present invention.

I claim:

1. An amorphous [6,7-bis(2-methoxy-ethoxy)-quinazolin-4-yl]-(3-ethynyl-phenyl)amine hydrochloride (erlotinib hydrochloride), wherein its X-ray powder diffraction pattern is substantially in accordance with FIG. 1.

2. A solid amorphous dispersion of erlotinib hydrochloride comprising erlotinib hydrochloride and a carrier, wherein the weight ratio of erlotinib hydrochloride to a carrier is from 1% to 300% and the carrier is selected from polyvinylpyrrolidone (PVP) or solid polyethylene glycol (PEG) and its X-ray powder diffraction pattern is substantially in accordance with FIG. 2.

3. A process for preparing solid amorphous dispersion of erlotinib hydrochloride and a carrier of claim 2, comprising the steps of dissolving erlotinib hydrochloride and a carrier into a solvent to form a solution and removing the solvent from the solution by distillation or by spray-drying at about 70-90° C. (outlet) and 140-170° C. (inlet), drying the product to afford solid amorphous dispersion, wherein the carrier is selected from polyvinylpyrrolidone (PVP) or solid polyethylene glycol (PEG).

4. A process for preparing amorphous erlotinib hydrochloride of claim 1, comprising the steps of dissolving crystalline erlotinib hydrochloride in a solvent to form a solution, and removing the solvent from the solution by distillation at about 40-75° C. or by spray-drying at about 35-60° C. (outlet) and 80-100° C. (inlet), and drying the product to afford amorphous form of erlotinib hydrochloride.

5. The process of claim 3 or 4, wherein the solvent is removed by distillation.

6. The process of claim 3 or 4, wherein the solvent is a $C_1$-$C_4$ alcohol, water or a mixture of water and ethanol.

7. The process of claim 6 wherein the $C_1$-$C_4$ alcohol is methanol, ethanol, n-propanol, isopropanol or branched-chain butanols or their mixtures.

8. The process of claim 3 or 4, wherein the preferred solvent is methanol, ethanol or a mixture of ethanol and water.

9. The process of claim 5 wherein the distillation is performed at a pressure of about 400 mm Hg or less.

10. The process of claim 5 wherein the distillation is performed at a pressure of from about 30 to about 80 mm Hg.

11. The process of claim 3 or 4, wherein the solvent is removed by spray drying.

12. The process of claim 11 wherein the spray drying is effected in the presence of an inert gas.

13. The process of claim 3 or 4, wherein the product obtained is dried at 35-45° C. under vacuum.

14. A pharmaceutical composition comprising amorphous erlotinib hydrochloride of claim 1 or 2, and a pharmaceutically acceptable excipient, diluent, additive, filler, lubricant, solvent, binder or stabilizer.

15. The pharmaceutical composition according to claim 14, wherein amorphous erlotinib hydrochloride is an amorphous form of erlotinib hydrochloride or solid amorphous dispersion of erlotinib hydrochloride and a carrier.

16. The pharmaceutical composition according to claim 15, wherein a carrier is polyvinylpyrrolidone (PVP) or solid polyethylene glycol (PEG).

17. The pharmaceutical composition according to claim 14, in the form of a tablet, troche, powder, syrup, patch, liposome, injection, dispersion, suspension, solutions, capsule, cream, ointment or aerosol.

* * * * *